US00PP36102P2

(12) United States Plant Patent
van Dijk

(10) Patent No.: US PP36,102 P2
(45) Date of Patent: Sep. 10, 2024

(54) ***HYDRANGEA* PLANT NAMED 'HIPEAR81'**

(50) Latin Name: *Hydrangea macrophylla*
Varietal Denomination: HIPEAR81

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 18/534,609

(22) Filed: Dec. 9, 2023

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

U.S. PATENT DOCUMENTS

PP34,547 P2 * 9/2022 van Dijk ..... Plt./250

* cited by examiner

*Primary Examiner* — Karen M Redden
(74) *Attorney, Agent, or Firm* — C. Anne Whealy

(57) ABSTRACT

A new and distinct cultivar of *Hydrangea* plant named 'HIPEAR81', characterized by its upright and broadly spreading plant habit; moderately vigorous and moderate growth rate; freely branching habit; strong and sturdy stems; dark green-colored leaves; freely flowering habit; large and dense mophead inflorescences with white-colored sterile flowers with purplish pink-colored margins; and good post-production longevity.

2 Drawing Sheets

Figure 1:
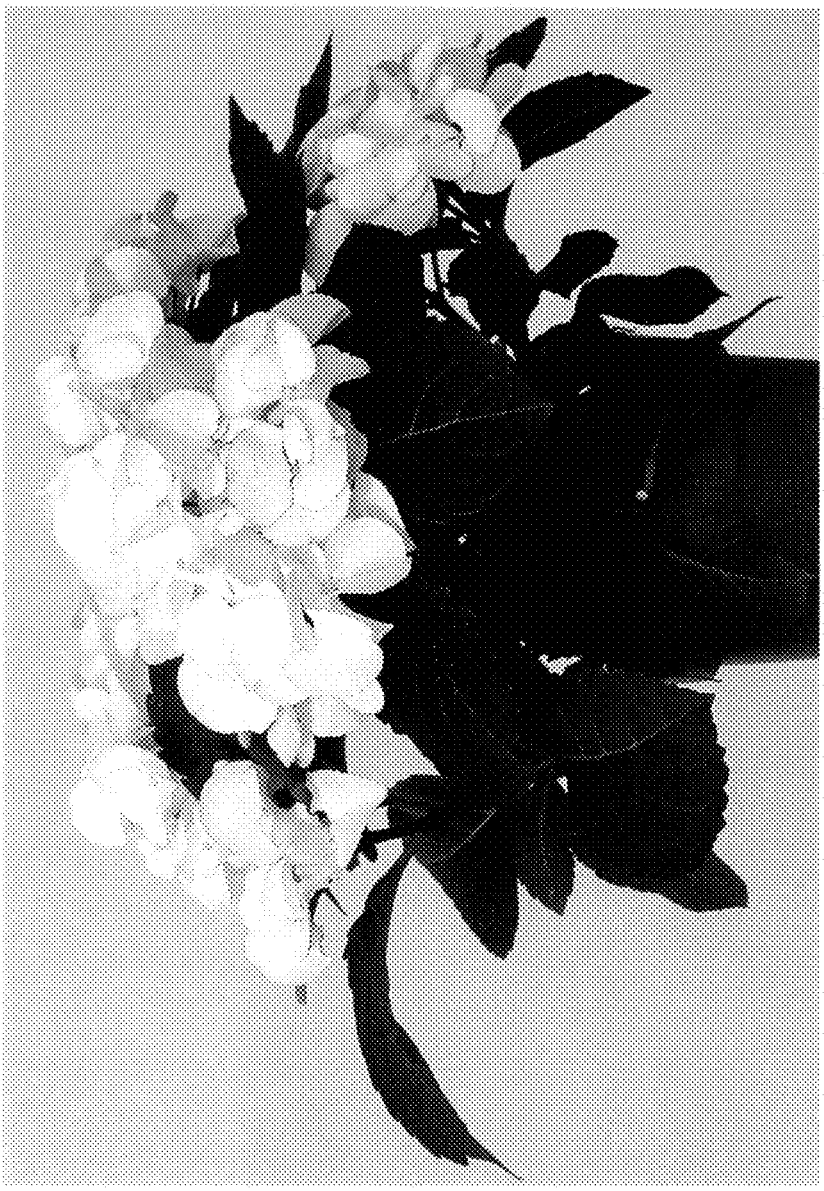

Botanical designation: *Hydrangea macrophylla.*
Cultivar denomination: 'HIPEAR81'.

STATEMENT REGARDING PRIOR DISCLOSURES BY INVENTOR/APPLICANT & ASSIGNEE

An United Kingdom Plant Breeder's Rights application for the instant plant was filed by the Assignee of the instant application, Hi Breeding B.V. of De Lier, The Netherlands on Nov. 11, 2022, application number 23/801. Foreign priority is not claimed to this United Kingdom Plant Breeder's Rights application.

An European Community Plant Breeder's Rights application for the instant plant was filed by the Assignee of the instant application, Hi Breeding B.V. of De Lier, The Netherlands on Jul. 4, 2023, application number 2023/1465. Foreign priority is not claimed to this European Plant Breeder's Rights application.

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIPEAR81'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination in April, 2017 of a proprietary selection of *Hydrangea macrophylla* identified as code number 1342, not patented, as the female, or seed, parent with a proprietary selection of *Hydrangea macrophylla* identified as code number 1213, not patented, as the male, or pollen, parent. The new *Hydrangea* plant was discovered and selected as a single flowering plant from within the progeny of the stated cross-pollination in a controlled greenhouse environment in De Lier, The Netherlands in April, 2019.

Asexual reproduction of the new *Hydrangea* plant by terminal vegetative cuttings since July, 2019 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIPEAR81'. These characteristics in combination distinguish 'HIPEAR81' as a new and distinct *Hydrangea* plant:

1. Upright and broadly spreading plant habit.
2. Moderately vigorous and moderate growth rate.
3. Freely branching habit.
4. Strong and sturdy stems.
5. Dark green-colored leaves.
6. Freely flowering habit.
7. Large and dense mophead inflorescences with white-colored sterile flowers with purplish pink-colored margins.
8. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* have sturdier stems than plants of the female parent selection.
2. Sterile flowers of plants of the new *Hydrangea* are white in color whereas sterile flowers of plants of the female parent selection are pale purple in color.

Plants of the new *Hydrangea* can be compared to plants of the male parent selection. Plants of the new *Hydrangea* differ primarily from plants of the male parent selection in the following characteristics:

1. Plants of the new *Hydrangea* have sturdier stems than plants of the male parent selection.
2. Sterile flowers of plants of the new *Hydrangea* are white in color whereas sterile flowers of plants of the male parent selection are light purple in color.

Plants of the new *Hydrangea* can be compared to plants of *Hydrangea macrophylla* 'HIICE', disclosed in U.S. Plant Pat. No. 34,566. In side-by-side comparisons, plants of the new *Hydrangea* differ primarily from plants of 'HIICE' in sterile flower color as sterile flowers of plants of the new *Hydrangea* are white in color with purplish pink-colored margins whereas sterile flowers of plants of 'HIICE' are pure white in color. In addition, stems of plants of the new *Hydrangea* are dark purple in color whereas stems of plants of 'HIICE' are medium green in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HIPEAR81' grown in a container.

Figure 2:
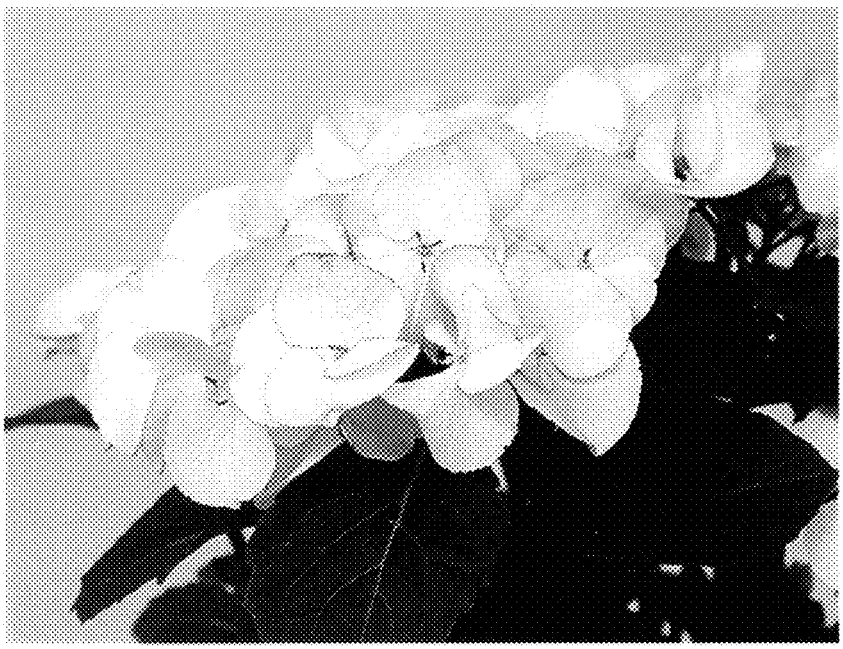

The photograph on the top of the second sheet (FIG. 2) is a close-up view of a typical flowering plant of 'HIPEAR81'.

DETAILED BOTANICAL DESCRIPTION

Plants used in the aforementioned photographs and in the following description were grown during the late summer in 13-cm containers in a glass-covered greenhouse in De Lier, The Netherlands and under cultural practices typical of commercial *Hydrangea* production. During the production of the plants, day temperatures ranged from 20C to 35C, night temperatures ranged from 10C to 22C and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used. As a white-colored *Hydrangea* plant, plants of the new *Hydrangea* are not treated with aluminum sulfate to "blue" the flower color.

Botanical description: *Hydrangea macrophylla* 'HIPEAR81'.

Parentage:

*Female, or seed, patent.*—Proprietary selection of *Hydrangea macrophylla* identified as code number 1342, not patented.

*Male, or pollen, patent.*—Proprietary selection of *Hydrangea macrophylla* identified as code number 1213, not patented.

Propagation:

*Type cutting.*—By vegetative terminal cuttings.

*Time to initiate roots, summer.*—About twelve days at temperatures about 22C.

*Time to initiate roots, winter.*—About 14 days at temperatures about 20C.

*Time to produce a rooted young plant, summer.*—About 28 days at temperatures about 22C.

*Time to produce a rooted young plant, winter.*—About 30 days at temperatures about 19C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright, broadly outwardly spreading and mounding plant habit; flattened globular in overall shape; strong and sturdy stems; moderately vigorous growth habit and moderate growth rate; about six months from propagation are required to produce small finished flowering plants.

*Plant height.*—About 23.8 cm.

*Plant diameter or area of spread.*—About 40.2 cm.

Lateral branch description:

*Branching habit.*—Freely branching habit with about ten lateral branches per plant; pinching enhances lateral branch development.

*Length.*—About 11.8 cm.

*Diameter.*—About 4 mm.

*Internode length.*—About 3.2 cm.

*Strength.*—Strong, sturdy.

*Aspect.*—About 10 to 90 degrees from vertical.

*Texture.*—Smooth, glabrous; becoming woody with development.

*Color, developing.*—Darker than a blend of N186B and N186C.

*Color, fully developed.*—Slightly darker than a blend of N186A and 203B; when woody, close to 200A to 200C.

*Lenticels.*—None observed.

Leaf description:

*Arrangement.*—Opposite, simple.

*Length.*—About 10.5 cm.

*Width.*—About 8.5 cm.

*Shape.*—Broadly ovate to broadly elliptic.

*Apex.*—Apiculate.

*Base.*—Short attenuate.

*Margin.*—Coarsely crenate-serrate.

*Texture, upper and lower surfaces.*—Slightly rugose, glabrous.

*Venation pattern.*—Pinnate.

*Color.*—Developing leaves, upper surface: Close to 143A Developing leaves, lower surface: Close to 143B. Fully developed leaves, upper surface: Slightly darker than NN137A; venation, close to 145C. Fully developed leaves, lower surface: Close to 137B to 137C; venation, close to 146C, proximally, occasionally tinged with close to 176A and 176B.

*Petioles.*—Length: About 1.3 cm. Diameter: About 3 mm to 3.5 mm. Texture and luster, upper and lower surfaces: Smooth, glabrous; slightly glossy. Color, upper surface: Close to 144B, occasionally margins, close to 177A. Color, lower surface: Close to 143C.

Flower description:

*Flower type and habit.*—Showy rotate sterile flowers and small, inconspicuous rotate fertile flowers arranged on mophead-type terminal panicles; panicles flattened globular in shape; sterile flowers face upright to outwardly, fertile flowers face mostly upright.

*Fragrance.*—None detected.

*Natural flowering season.*—In the garden, plants flower continuously from the late spring to late summer in The Netherlands; flower dormancy can be broken with a cold storage treatment.

*Flower longevity.*—Good postproduction longevity; sterile flowers maintain good substance for about six weeks on the plant, sterile flowers persistent; fertile flowers last for a few days on the plant, fertile flowers not persistent.

*Quantity of flowers.*—Freely flowering habit; about 45 sterile flowers per panicle and about 25 fertile flowers per panicle.

*Panicle height.*—About 10 cm.

*Panicle diameter.*—About 15.1 cm.

*Panicle peduncles.*—Length: About 7.9 cm. Diameter: About 3 mm. Strength: Strong. Aspect: Primary peduncles, mostly erect; lateral peduncles, about 30 degrees from primary peduncle axis. Texture: Moderately pubescent. Color: Close to a blend of N186C and 203A.

*Sterile flower buds.*—Length: About 1.1 cm. Diameter: About 2 cm. Shape: Broadly cup-shaped. Color: Close to 157A and towards the margins and apex, close to 145C.

*Fertile flower buds.*—Length: About 5 mm. Diameter: About 5 mm. Shape: Broadly obovate. Color: Close to N155B.

*Sterile flower diameter.*—About 3.9 cm to 5.8 cm.

*Sterile flower depth* (*height*).—About 1.8 cm to 3.2 cm.

*Fertile flower diameter.*—About 5 mm.

*Fertile flower depth* (*height*).—About 7 mm.

*Petals, sterile flowers.*—Quantity and arrangement: Four, occasionally, five, in a single whorl. Length: About 3 mm. Width: About 2.75 mm. Shape: Broadly ovate, concave. Apex: Acute. Base: Cuneate. Margin: Entire. Texture and luster, upper and lower surfaces: Smooth, glabrous; matte. Color: When opening and fully opened, upper surface: Close to N155A with narrow margins, close to 63C and apices, close to 63A; color does not change with subsequent development. When opening and fully opened, lower surface: Close to NN155D flushed with close to 60D; midvein, close to 60C; color does not change with subsequent development.

*Petals, fertile flowers.*—Quantity and arrangement: About five in a single whorl. Length: About 3 mm. Width: About 2.75 mm. Shape: Broadly ovate, slightly concave. Apex: Acute. Base: Cuneate. Margin: Entire. Texture and luster, upper and lower surfaces: Smooth, glabrous; matte. Color: When opening and fully opened, upper surface: Close to N155A with narrow margins, close to 63C and apices, close to 63A; color does not change with subsequent development. When opening and fully opened, lower surface: Close to NN155D flushed with close to 60D; midvein, close to 60C; color does not change with subsequent development.

*Sepals, sterile flowers.*—Quantity and arrangement: Typically three or four, occasionally two or five, in a single whorl; strongly imbricate. Length: About 1.9 cm to 3 cm. Width: About 2.1 cm to 4.3 cm. Shape: Reniform to broadly reniform; slightly concave. Apex: Obtuse to shallowly retuse. Base: Truncate to broadly cuneate. Margin: Shallowly crenate to shallowly crenate-dentate; slightly coarsely undulate. Texture and luster, upper and lower surfaces: Smooth, glabrous; matte. Color: When opening, upper surface: Close to 155A to 155B and towards the base, close to 150D and apex, close to 63C. When opening, lower surface: Close to 157D and towards the margins and base, close to 157B; apical narrow margins, close to 63B; midvein, close to 63B. Fully opened, upper surface: Close to NN155D; narrow margins and apex, close to 63C; color does not change with subsequent development. Fully opened, lower surface: Close to NN155D; narrow margins and apex, close to 64C; venation, close to 64C; color does not change with subsequent development.

*Sepals, fertile flowers.*—Quantity and arrangement: Five in a single whorl. Length: About 2 mm. Width: About 1.75 mm. Shape: Broadly ovate. Apex: Acute. Base: Cuneate. Margin: Entire. Texture and luster, upper and lower surfaces: Smooth, glabrous; matte. Color: When opening and fully opened, upper surface: Close to 157A with apices, close to 144A; color does not change with subsequent development. When opening and fully opened, lower surface: Close to 144A; color does not change with subsequent development.

*Pedicels, sterile flowers.*—Length: About 2.4 cm. Diameter: About 2 mm. Strength: Moderately strong. Aspect: About 30 degrees from main peduncle axis. Texture and luster: Moderately pubescent; slightly glossy. Color: Close to 187B and distally, close to 59C.

*Pedicels, fertile flowers.*—Length: About 6 mm. Diameter: About 0.75 mm. Strength: Moderately strong. Aspect: About 10 degrees from vertical. Texture and luster: Sparsely pubescent; matte. Color: Close to 186A.

*Reproductive organs, sterile flowers.*—Stamens: Quantity per flower: About eight, occasionally, ten. Filament length: About 3 mm. Filament color: Close to NN155D. Anther length: About 1 mm. Anther shape: Broadly oblong. Anther color: Close to 157D. Pollen amount: Moderate. Pollen color: Close to 155A. Pistils: Pistil quantity per flower: About two, occasionally, three. Pistil length: About 1.75 mm. Stigma shape: Club-shaped. Stigma color: Close to NN155D. Style length: About 1 mm. Style color: Close to 157D. Ovary color: Close to 157D.

*Reproductive organs, fertile flowers.*—Stamens: Quantity per flower: About ten, occasionally, eight. Filament length: About 3 mm. Filament color: Close to NN155D. Anther length: About 1 mm. Anther shape: Broadly oblong. Anther color: Close to 157D. Pollen amount: Moderate. Pollen color: Close to 155A. Pistils: Pistil quantity per flower: About three, occasionally two. Pistil length: About 2 mm. Stigma shape: Club-shaped. Stigma color: Close to NN155D. Style length: About 1.25 mm. Style color: Close to 157D. Ovary color: Close to 157D.

*Seeds.*—To date, seed development has not been observed on plants of the new *Hydrangea.*

Pathogen & pest resistance: Plants of the new *Hydrangea* have been observed to be tolerant to *Botrytis* (*Botrytis cinerea*). To date, plants of the new *Hydrangea* have not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIPEAR81' as illustrated and described.

* * * * *